US006509196B1

(12) United States Patent
Brooks et al.

(10) Patent No.: US 6,509,196 B1
(45) Date of Patent: Jan. 21, 2003

(54) COMPENSATION FOR NON-SPECIFIC SIGNALS IN QUANTITATIVE IMMUNOASSAYS

(75) Inventors: Donald Elliott Brooks, Vancouver (CA); Paul C. Harris, Bothell, WA (US); Andrew D. Olal, Burnaby (CA); Zongcen Charles Xie, Burnaby (CA); Brian G. Richards, North Vancouver (CA)

(73) Assignee: Response Biomedical Corp., Burnaby (CA)

( * ) Notice: Subject to any disclaimer, the term of this patent is extended or adjusted under 35 U.S.C. 154(b) by 0 days.

(21) Appl. No.: 09/477,103

(22) Filed: Jan. 4, 2000

(51) Int. Cl.$^7$ ............................................. G01N 33/558
(52) U.S. Cl. ........................... 436/514; 422/55; 422/56; 422/57; 422/58; 422/61; 435/7.1; 435/287.1; 435/287.2; 435/287.9; 435/287.7; 435/805; 435/810; 435/970; 436/518; 436/169; 436/805; 436/810
(58) Field of Search ............................... 422/55–58, 61; 435/7.1, 287.1, 287.2, 287.9, 287.7, 805, 810, 970; 436/514, 518, 169, 805, 810

(56) References Cited

U.S. PATENT DOCUMENTS

| 5,356,782 A | 10/1994 | Moorman et al. ............ 435/7.9 |
| 5,384,264 A | 1/1995 | Chen et al. .................. 436/525 |
| 5,458,852 A | 10/1995 | Buechler ..................... 422/58 |
| 5,506,114 A | 4/1996 | Sangha ........................ 435/15 |
| 5,569,589 A | 10/1996 | Hiaoka et al. ............... 435/7.9 |
| 5,569,608 A | 10/1996 | Sommer ..................... 436/518 |
| 5,610,077 A | 3/1997 | Davis et al. ................ 436/518 |
| 5,622,871 A | 4/1997 | May et al. .................. 436/514 |
| 5,648,274 A | 7/1997 | Chandler .................... 436/514 |
| 5,656,503 A | 8/1997 | May et al. .................. 436/514 |
| 5,753,517 A | 5/1998 | Brooks et al. .............. 436/514 |
| 5,885,527 A | 3/1999 | Buechler ..................... 422/58 |

FOREIGN PATENT DOCUMENTS

| EP | 0 093 613 | 11/1983 |
| WO | WO 88/08534 | 11/1988 |
| WO | WO 93/03175 | 2/1993 |
| WO | WO 97/09620 | 3/1997 |

OTHER PUBLICATIONS

Reeves, S.G. and Durst, R.A., "Novel Optical Measurement Approach for the Quantitation of Liposome Immunomigration Assay," *Analytical Letters*, 28 (13):2347–2362 (1995).
Melamies, L., et al., "Evaluation of a Quantitative Photometric Latex Agglutination Immunoassay for α–Foetoprotein," *J. Clin. Chem. Clin. Biochem.*, 25 (3):173–176 (1987).
Abe, J., et al., "Rapid Quantitation of Serum Myoglobin by Latex Agglutination Turbidimetry," *Clinića Chimica Acta*, 203:95–96 (1991).

Borque, L., et al., "Automated Quantitative Nephelometric Latex Immunoassay for Determining Ferritin in Human Serum," *J. Clin. Lab. Analysis*, 6:239–244 (1992).
Roberts, M.A. and Durst, R.A., "Investigation of Liposome--Based Immunomigration Sensors for the Detection of Polychlorinated Biphenyls," *Anal. Chem.*, 67(3):482–491 (1995).
Siebert, S.T.A., et al., "Liposome Immunomigration Field Assay Device for Alachlor Determination," *Analytica Chimica Acta*, 282:297–305 (1993).
Siebert, S.T.A., et al., "Improved Liposome Immunomigration Strip Assay for Alachlor Determination," *Analytica Chimica Acta*, 311;309–318 (1995).
Schifreen, R.S., et al., "A Quantitative Automated Immunoassay for Fibrinogen/Fibrin Degradation Products," *Clin. Chem.*, 31(9):1468–1473 (1985).
Laitinen, M.P.A. and Vuento, M., "Immunochromatographic Assay for Quantitation of Milk Progesterone," *Acta Chemica Scandinavica*, 50:141–145 (1996).

*Primary Examiner*—Christopher L. Chin
(74) *Attorney, Agent, or Firm*—Hamilton, Brook, Smith & Reynolds, P.C.

(57) ABSTRACT

Methods for quantitatively measuring the amount of an analyte of interest in a fluid sample are disclosed. The methods involve providing a membrane having an application point, a detection zone, and a contact region, where the contact region is between the application point and the detection zone, and has test particles and internal control particles imbedded within it; contacting the application point with the fluid sample; maintaining the membrane under conditions sufficient to allow fluid to transport analyte by capillary action to the contact region, where the analyte binds to the test particles; further maintaining the membrane under conditions sufficient to allow fluid to transport analyte-bound test particles and internal control particles to the detection zone, where they interact with a detection reagent; and detecting the amount of test particles and the amount of internal control particles in the detection zone. The amount of analyte in the fluid sample is related to a corrected test particle amount, which can be determined, for example, as the difference between the amount of test particles and the amount of internal control particles in the detection zone. Alternatively, the fluid sample can be contacted with the detection zone of the apparatus, and the test particles are mobilized by addition of fluid to the application point. Other methods involve providing a solid phase reactant for an enzyme-linked immunosorbent assay, and contacting the solid phase reactant with a solution containing an initial detection antibody and an internal control antibody. The amount of analyte in the fluid sample is related to a corrected amount of initial detection antibody, which can be determined, for example, as the difference between the amount of initial detection antibody and the amount of internal control antibody on the solid-phase reactant.

8 Claims, No Drawings

COMPENSATION FOR NON-SPECIFIC SIGNALS IN QUANTITATIVE IMMUNOASSAYS

BACKGROUND OF THE INVENTION

Quantitative analysis of cells and analytes in fluid samples, particularly bodily fluid samples, often provides critical diagnostic and treatment information for physicians and patients. Quantitative immunoassays utilize the specificity of the antigen (Ag)—antibody (Ab) reaction to detect and quantitate the amount of an Ag or Ab in a sample. In solid phase immunoassays, one reagent (e.g., the Ag or Ab) is attached to a solid surface, facilitating separation of bound reagents or analytes from free reagents or analytes. The solid phase is exposed to a sample containing the analyte, which binds to its Ag or Ab; the extent of this binding is quantitated to provide a measure of the analyte concentration in the sample. Transduction of the binding event into a measurable signal, however, is affected by a number of interferences, such as non-specific binding of components of the assay to the solid phase, which are not associated with the presence or amount of the analyte. These interferences limit the specificity and applicability of quantitative immunoassays.

SUMMARY OF THE INVENTION

The invention relates to methods of measuring the amount of an analyte of interest in a fluid sample, using a solid phase assay such as a quantitative immunochromatographic assay or an enzyme-linked immunosorbent assay, in which an internal control is used to compensate for non-specific binding of assay components.

For a quantitative immunochromatographic assay, the methods use a membrane strip made of a suitable material, such as cellulose nitrate or glass fiber, which has sufficient porosity and the ability to be wet by the fluid containing the analyte, and which allows movement of particles by capillary action. The membrane strip has an application point, a contact region, and a detection zone; the contact region is between the application point and the detection zone. Imbedded in the contact region is a population of test particles, such as liposomes or organic polymer latex particles, and a population of internal control particles of the same type. The test particles are coated with a binding agent (e.g., an antibody) to the analyte of interest, and the internal control particles are coated with a binding agent (e.g., an antibody) to a control analyte. The particles can be labeled, using a colorimetric, fluorescent, luminescent, or other appropriate label, to facilitate detection; test particles and internal control particles are labeled using distinguishable labels, preferably of the same type (e.g., two distinguishable fluorescent labels). A detection reagent (e.g., antibody to the analyte of interest) is immobilized in the detection zone.

In the methods, the application point of the membrane strip is contacted with the fluid sample to be assayed for the analyte of interest. The membrane strip is then maintained under conditions which are sufficient to allow capillary action of fluid to transport the analyte of interest, if analyte is present in the sample, through the membrane strip to the contact region. The apparatus is further maintained so that when analyte of interest reaches the contact region, the analyte binds to the analyte binding agent coated on the test particles imbedded in the contact region. Test particles, including those which are bound with analyte, as well as internal control particles, are mobilized by fluid and move by capillary action through the strip to the detection zone. The detection reagent interacts with analyte-bound test particles; interaction of the detection reagent and the analyte-bound test particles results in arrest of analyte-bound test particles in the detection zone. The amount of test particles that are arrested in the detection zone is then detected, as is the amount of internal control particles in the detection zone. The amount of non-specific binding of test particles that are arrested in the detection zone is approximated by the amount of non-specific binding of internal control particles in the detection zone. Thus, the amount of analyte of interest in the fluid sample can be more accurately determined by eliminating the non-specific binding component: for example, the amount of analyte of interest in the fluid sample can be determined as the difference between the amount of test particles that are arrested in the detection zone and the amount of internal control particles that are arrested in the detection zone. The amount of analyte can determined from a standard curve for the analyte of interest.

If desired, the membrane strip can also comprise a control reaction zone, having control detection reagent coated on the membrane. The internal control particles are coated with a binding agent (e.g., an antibody) to the control detection reagent. Capillary action of the fluid mobilizes the internal control particles not only to the detection zone, but also to the control reaction zone, where they bind to the control detection reagent. The amount of analyte of interest in the fluid sample is determined by taking into consideration the amount of test particles that are non-specifically arrested in the detection zone, represented by the amount of internal control particles that are arrested in the detection zone. For example, the amount of analyte of interest in the fluid sample can be determined as a ratio between 1) the difference between the amount of test particles that are arrested in the detection zone and the amount of internal control particles that are arrested in the detection zone, and 2) the amount of internal control particles in the control reaction zone.

In an alternative immunochromatographic assay, the fluid sample to be assayed for the analyte of interest is applied directly to the detection zone of the apparatus. In this embodiment, the detection reagent is antibody to the analyte of interest. The membrane strip is maintained under appropriate conditions so that analyte in the fluid sample interacts with the detection reagent, and is immobilized in the detection zone. Water or an appropriate buffer is then added to the application point of the membrane, to mobilize the test particles and the internal control particles, which are moved by capillary action into the detection zone. The membrane strip is further maintained under conditions which allow interaction of the test particles with analyte that is immobilized in the detection zone. Interaction of the test particles with immobilized analyte arrests movement of the test particles. The amount of analyte in the fluid sample is determined by taking into consideration the amount of test particles that are non-specifically arrested in the detection zone; for example, the amount of analyte can be related to the difference between the amount of test particles that are arrested in the detection zone, and the amount of internal control particles that are arrested in the detection zone, and can be determined from a standard curve, as described above.

For an enzyme-linked immunosorbent assay, a solid phase reactant (e.g., a microtiter plate) having a first member of an immunobinding pair, such as an analyte-binding agent (e.g., antibody) to the analyte of interest adsorbed thereon, is contacted with a sample to be assayed for the amount of a second member of the immunobinding pair, such as an analyte of interest, under conditions allowing the members of the immunobinding pair to interact (e.g., to allow analyte of interest to bind to the analyte-binding agent, such as antibody, adsorbed on the solid phase reactant). Alternatively, a solid phase reactant having a test sample to be assayed for the amount of a first member of an immunobinding pair adsorbed thereon, is contacted with a solution containing the second member of the immunobiding pair, under conditions allowing the members of the immunobinding pair to interact. The solid phase reactant is then contacted with a solution containing an initial detection antibody and an internal control antibody, under conditions allowing the initial detection antibody to bind to the second member of the immunobinding pair that is bound to the first member of the immunobinding pair adsorbed on the solid phase reactant. The amount of initial detection antibody on the solid phase reactant, and the amount of internal control antibody on the solid phase reactant, are then determined; the amount of the first (or second) member of the immunobinding pair is determined by taking into consideration the amount of each member of the immunobinding pair that is non-specifically arrested, as shown by the amount of internal control antibody that is bound. For example, the difference can be determined between amount of initial detection antibody on the solid phase reactant, and the amount of internal control antibody on the solid phase reactant.

The methods of the current invention compensate for variations in the structure of the solid phase reactants as well as other factors which can contribute to non-specific binding of components of the assays, thereby allowing more accurate determination of the amounts of analytes of interest in solutions.

DETAILED DESCRIPTION OF THE INVENTION

The current invention pertains to methods of correcting for non-specific binding of reagents in quantitative, solid-phase, immunoassays. As described herein, Applicants have developed a means for compensating for non-specific binding of components of an immunoassay to the solid phase of the assay, thereby enhancing the accuracy of the measurement of the amount of analyte of interest. The methods involve inclusion, within the immunoassay, of an internal control reagent (internal control particles) that interact with the solid surfaces of the immunoassay in the same manner as the test particles used to detect the analyte of interest. The behavior of the internal control particles is used to provide an approximation of the amount of non-specific reaction of the test particles with the surfaces of the immunoassay. The amount of non-specific reaction of the test particles can then be taken into consideration in a determination of the amount of analyte of interest, thereby allowing a more accurate determination of the amount of specific reaction of test particles. For example, subtraction of the signal resulting from the non-specific reaction (e.g., as approximated by the amount of internal control particles) from the signal resulting from the total reaction of the test particles (which includes both specific and non-specific reaction of test particles), or another appropriate calculation to eliminate the non-specific component of the reaction, compensates for the non-specific binding in the determination of the amount of analyte of interest.

An "immunoassay," as the term is used herein, refers to an in vitro procedure for analysis of a sample to determine the presence, absence, or quantity of one or more analytes, preferably utilizing antibodies as a component of the procedure. In a preferred embodiment, the immunoassays is quantitative immunochromatographic assay, which is a test for an analyte in which a fluid test sample containing analyte is contacted with a membrane having imbedded within it particles coated with an analyte-binding agent, such as antibodies to the analyte, causing capillary action of components of the system through the membrane, with a positive result indicated by detection of interaction between binding agent-coated particles and the analyte in a detection zone of the membrane, the amount of binding agent-coated particles in the detection zone being related to the amount of analyte in the test sample. For representative quantitative immunochromatographic assays, see, for example, U.S. Pat. No. 5,753,517, the entire teachings of which is incorporated by reference herein.

The term, "analyte," as used herein, refers to the molecule or compound for which the amount will be measured. Examples of analytes include proteins, such as hormones or enzymes; glycoproteins; peptides; small molecules; polysaccharides; antibodies; nucleic acids; drugs; toxins; viruses or virus particles; portions of a cell wall; and other compounds. The analyte is "immunogenic," which indicates that antibodies (as described below) can be raised to the analyte. In one embodiment, the analyte is myoglobin. The analyte is in a fluid sample. The fluid sample can be a fluid having relatively few components, for example, an aqueous solution containing the analyte of interest; alternatively, the fluid sample can be a fluid having many components, such as a complex biological fluid (e.g., whole blood, plasma, serum, urine, cerebrospinal fluid, or other biological fluid). In a preferred embodiment, if the analyte of interest is myoglobin, the fluid sample is whole blood, plasma or serum. The "analyte binding agent," as used herein, refers to a compound that specifically binds to the analyte, such as an antibody, a hapten or drug conjugate, a receptor, or another binding partner. An analyte binding agent that specifically binds to an analyte of interest is an agent that preferentially binds to the analyte of interest, preferably to the exclusion of any binding to another compound in the assay. In a preferred embodiment, the analyte binding agent is an antibody to the analyte of interest.

Quantitative Immunochromatographic Assay

In one embodiment of the invention, a quantitative immunochromatographic assay, such as that described in U.S. Pat. No. 5,753,517, is performed. In such a quantitative immunochromatographic assay, a solid phase, such as a rapid antigen measurement platform (RAMP™.) apparatus (U.S. Pat. No. 5,753,517), is used. The solid phase includes a membrane strip having an application point, a contact region, and a detection zone. The membrane strip can be made of a substance having the following characteristics: sufficient porosity to allow capillary action of fluid along its surface and through its interior; the ability to allow movement of coated particles by capillary action (i.e., it must not block the particles); and the ability to be wet by the fluid containing the analyte (e.g., hydrophilicity for aqueous fluids, hydrophobicity for organic solvents). Hydrophobicity of a membrane can be altered to render the membrane hydrophilic for use with aqueous fluid, by processes such as those described in U.S. Pat. No. 4,340,482, or U.S. Pat. No. 4,618,533, which describe transformation of a hydrophobic surface into a hydrophilic surface. Examples of membrane substances include: cellulose, cellulose nitrate, cellulose acetate, glass fiber, nylon, polyelectrolyte ion exchange membrane, acrylic copolymer/nylon, and polyethersulfone. In a preferred embodiment, the membrane strip is made of cellulose nitrate.

The "application point" is the position on the membrane where a fluid sample is applied. The "contact region" of the membrane is adjacent to the application point. Imbedded in the "contact region" of the membrane is a population of "test particles" which are coated with analyte binding agent, such as antibodies (or other types of molecules that specifically bind) to the analyte of interest. The population of particles varies, depending on the size and composition of the particles, the composition of the membrane, and the level of sensitivity of the assay. The population typically ranges approximately between $1 \times 10^3$ and $1 \times 10^9$ particles, although fewer or more can be used if desired. In a preferred embodiment, the population is approximately $2 \times 10^7$ particles.

The test particles are particles which can be coated with analyte binding agent, such as antibodies or with other agents that specifically bind to the analyte. In a preferred embodiment, the test particles are liposomes, organic polymer latex particles, inorganic fluorescent particles or phosphorescent particles. In a particularly preferred embodiment, the particles are polystyrene latex beads, and most particularly, polystyrene latex beads that have been prepared in the absence of surfactant, such as surfactant-free Superactive Uniform Aldehyde/Sulfate Latexes (Interfacial Dynamics Corp., Portland, Oreg.).

The size of the particles is related to porosity of the membrane: the particles must be sufficiently small to be transported along the membrane by capillary action of fluid. The particles can be labeled to facilitate detection. The particles are labeled by a means which does not significantly affect the physical properties of the particles; for example, the particles are labeled internally (that is, the label is included within the particle, such as within the liposome or inside the polystyrene latex bead). Representative labels include luminescent labels; phosphorescent labels; and colorimetric labels, such as dyes or fluorescent labels. In a preferred embodiment, a fluorescent label is used. In another preferred embodiment, phosphorescent particles are used, particularly "up-converting" phosphorescent particles, such as those described in U.S. Pat. No. 5,043,265.

The particles are coated with an agent that specifically binds to the analyte of interest. In a preferred embodiment, the particles are coated with antibodies to the analyte of interest. The antibodies can be monoclonal antibodies or polyclonal antibodies. The term "antibody", as used herein, also refers to antibody fragments which are sufficient to bind to the analyte of interest. Alternatively, molecules which specifically bind to the analyte of interest, such as engineered proteins having analyte binding sites, can also be used (Holliger, P. and H. R. Hoogenbloom, Trends in Biotechnology 13:7–9 (1995); Charnow, S. M. and A. Ashkenazi, Trends in Biotechnology 14:52–60:1996)). In another embodiment, if the analyte of interest is a drug, a hapten or other drug conjugate can be used as the analyte binding agent. Alternatively, in another embodiment, a receptor which binds to the analyte can be used if the analyte of interest is a ligand. If the analyte is an antibody of known specificity, the particles can be coated with the antigen against which the analyte-antibody is directed, or can be coated with antibody to the analyte-antibody.

Also imbedded in the "contact region" of the membrane is a population of "internal control particles." The internal control particles are identical to the test particles, in that they are particles of the same type, size and surface properties as the test particles; in a preferred embodiment, the internal control particles are from the same manufacturer's batch of particles as the test particles. The internal control particles are coated with a control analyte binding agent that is comparable to the agent coated on the test particles. For example, if the test particles are coated with antibodies, the internal control particles are also coated with antibodies. Alternatively, if the test particles are coated with antigen, the internal control particles are also coated with an antigen (control antigen) which has similar properties (e.g., size, composition, etc.) to the antigen coated on the test particles. In a preferred embodiment, the analyte binding agent is an antibody to the analyte; and the control analyte binding agent is an antibody that binds to an uninvolved antigen or analyte (that is, an antigen or analyte that does not interact with the analyte of interest or with the antibody coated on the test particles). The target of the internal control binding agent (e.g., the antigen for the antibody used as an internal control agent) is also referred to herein as the "control detection reagent," particularly when a control reaction zone and control detection reagent are used as described below. The internal control particles are coated with the same surface concentration of control analyte binding agent (e.g., antibody or other agent) as the test particles. In a preferred embodiment, the test particles and the internal control particles are both coated with antibodies; in a particularly preferred embodiment, the antibodies on the test particles and on the internal control particles are both of the same class and isotype (e.g., both are IgG antibodies). The internal control particles can be labeled to facilitate detection. They are labeled by the same means as the test particles (e.g., luminescent labels, calorimetric labels (e.g., fluorescent labels), or phosphorescent labels, depending on the label used for the test particles). In a preferred embodiment, both the test particles and the internal control particles are labeled with a fluorescent label, and the fluorescent labels for the test particles and for the internal control particles are distinguishable from one another. In another preferred embodiment, both the test particles and the internal control particles are phosphorescent particles which are capable of being "up-converted" to emit distinguishable colors.

The contact region of the membrane is between the application point and the "detection zone" of the membrane. The detection zone refers to a point on the membrane strip at which a "detection reagent" is immobilized. The detection reagent is an analyte binding agent, such as antibody directed against the same epitope of the analyte, or against a different epitope of the analyte, as antibodies coated onto the particles. Alternatively, the detection reagent can be the analyte of interest itself.

If desired, the apparatus can additionally include additional internal control features, such as a control detection reagent, and a control reaction zone. The "control detection reagent" can be a reagent which does not interact with either the analyte to be measured, the analyte binding agent on the analyte binding agent-coated particles, or the detection reagent. Alternatively, the control detection reagent can be an agent which interacts with the analyte binding agent, provided that it does not interact with the analyte itself. For example, if the analyte binding agent is an antibody, the control detection reagent can be an anti-immunoglobulin antibody. In a preferred embodiment, the analyte binding agent is an antibody, and the control detection reagent is an antiimmunoglobulin antibody; an anti-immunoglobulin antibody binds to the internal control particles in a manner that is essentially the same as the manner in which the antibody (analyte binding agent) binds to the analyte. In this embodiment, the particles (both test and internal control) are expected to behave in a similar manner as they are arrested, thereby minimizing the impact of any differences on the reaction. The control detection reagent is coated on the membrane in a "control reaction zone," which is a point on the membrane strip at which the control detection reagent is immobilized. The control reaction zone can be between the contact region and the detection zone; alternatively, the detection zone can be between the contact region and the control reaction zone.

To perform the quantitative immunochromatographic assay, a fluid sample containing the analyte of interest is obtained. The fluid can be a fluid that wets the membrane material; that supports a reaction between the analyte of interest and the analyte binding agent, such as the antibody/antigen reaction (i.e., does not interfere with antibody/antigen interaction); and that has a viscosity that is sufficiently low to allow movement of the fluid by capillary action. In a preferred embodiment, the fluid is an aqueous solution (such as a bodily fluid).

In a first embodiment of the quantitative immunochromatographic assay, the application point of the membrane strip is contacted with the fluid sample to be assayed for the analyte of interest. After the membrane strip is contacted with the fluid sample containing the analyte of interest at the application point, the membrane strip is maintained under conditions which allow fluid to transport the analyte by capillary action to the "contact region" of the membrane. When the analyte is transported to the Acontact region, analyte that is present in the fluid (if any is present) binds to the test particles imbedded in the contact region. "Binding" of analyte to the test particles indicates that the analyte binding agent coated onto the particle is bound to analyte of interest. A test particle which is "insufficiently bound" is one at which the binding sites of the analyte binding agents coated onto the particle are not completely filled by the analyte of interest, such that binding agent on the particle is capable of binding to additional analyte. A test particle which is insufficiently bound to analyte of interest, as described herein, can be bound to some analyte, or to no analyte. If no further analyte can be bound to the test particle, the analyte binding agent-coated particle is said to be "saturated" with analyte. Test particles which have been maintained under conditions allowing analyte in the fluid to bind to the test particles imbedded in the contact region are referred to herein as "contacted test particles". Contacted test particles may or may not have analyte bound to the analyte binding agent, depending on whether or not analyte is present in the fluid sample and whether analyte has bound to the analyte binding agent on the test particles. Thus, the population of contacted test particles may comprise particles having analyte bound to the analyte binding agent, as well as particles having no analyte bound to the analyte binding agent Oust as the test particles initially have no analyte bound to the analyte binding agent).

Capillary action of the fluid from the fluid sample mobilizes the contacted test particles, and the internal control particles, and moves the contacted test particles and internal control particles along the membrane to a "detection zone" on the membrane and to the "control reaction zone" as well, if it is present. If a control reaction zone is present, the membrane strip is maintained under conditions (e.g., sufficient time) which allow the internal control particles to move by capillary action along the membrane to both the detection zone and to the control reaction zone, regardless of the sequence of their placement on the membrane strip: that is, the internal control particles may reach the detection zone first, if it is between the contact region and the control reaction zone; alternatively, the internal control particles may reach the control reaction zone first, if it is between the contact region and the detection zone.

The movement of contacted test particles is arrested by binding to the detection reagent, and the movement of internal control particles is arrested by binding to the control detection reagent in the control reaction zone, if it is present. Alternatively, in one embodiment in which the control analyte binding agent is antibody to uninvolved antigen and the analyte binding agent is antibody to the analyte of interest, the control detection reagent can be antibody against immunoglobulin of the species from which the analyte binding agent and control analyte binding agent are derived. In this embodiment, the antibody to immunoglobulin should be non-cross reactive with other components of the sample: for example, if a human sample is being tested, an antibody that does not react with human immunoglobulin can be used as the control detection reagent. If an antibody to immunoglobulin is used, arrest of both control and test particles occurs at the control reaction zone. The arrest of both types of particles does not interfere with detection of the amount of each type of the particles at each zone, as different labels are used as described above.

The detection reagent binds to contacted test particles by binding to analyte which is bound to analyte binding agent on the contacted test particles, or by binding to analyte binding agent itself. The term, "detection-reagent-particle complexes", as used herein, refers to a complex of the detection reagent and contacted test particles. The detection-reagent-particle complexes are arrested (e.g., immobilized) in the detection zone. different labels are used as described above.

The amount of test particles arrested in the detection zone is then detected. The amount of test particles arrested in the detection zone includes not only those test particles which form part of detection-reagent-particle complexes, but also those test particles that are present due to non-specific arrest of the test particles in the detection zone. The test particles are detected using an appropriate means for the type of label used on the test particles. The amount of internal control particles arrested in the detection zone is also detected separately (that is, the amounts are measured individually, and not as a combination of amount of test particles and internal control particles). In a preferred embodiment, the amount of test particles is detected by an optical method, such as by measuring the light scattering in the detection zone, or by measuring the amount of fluorescence of the label of the test particles and the internal control particles.

The amount of analyte in the fluid sample is then determined, based on the amount of test particles arrested in the detection zone and the amount of internal control particles arrested in the detection zone. In one embodiment, the amount of test particles and the amount of internal control particles imbedded in the contact region prior to performing the assay are approximately equal. When the amount are approximately equal, the amount of internal control particles in the detection zone provides an approximation of (is approximately equal to) the amount of non-specifically arrested test particles in the detection zone. The amount of non-specifically arrested test particles (which is equated with the amount of internal control particles in the detection zone) is included in the determination of a "corrected test particle amount". For example, if the analyte binding agent and the control analyte binding agent are both antibodies, the corrected test particle amount is equal to the difference between the amount of test particles arrested in the detection zone and the amount of internal control particles in the detection zone.

If the amounts of test particles and internal control particles in the contact region are not equal, a series of calibration experiments can be run in which the amount of test particles and internal control particles arrested in the detection zone in the absence of analyte, as described herein, are measured over the range of particle concentrations of interest. The amount of test particles non-specifically arrested in the detection zone can then be determined, for example, from a standard curve plotting the relationship between the amount of test particles and the amount of internal control particles arrested in the detection zone. Then the amount of non-specifically arrested test particles can be used in a determination of the corrected test particle amount. For example, the amount of non-specifically arrested test particles can be subtracted from the amount of test particles in the detection zone to generate a corrected test particle amount.

The amount of analyte of interest in the fluid sample is related to, and can be determined from, the corrected test particle amount. For example, the amount of analyte of interest can be determined through the use of a standard curve. The standard curve is generated by preparing a series of control samples, containing known concentrations of the analyte of interest in the fluid in which the analyte is to be detected (such as serum depleted of the analyte). The quantitative immunochromatographic assay is then performed on the series of control samples; the amount of detection-reagent-particle complexes and the amount of internal control particles in the detection zone are measured for each control sample; the corrected test particle amounts are determined; and the corrected test particle amounts are plotted as a function of the concentration of analyte included in the control sample. Samples containing an unknown amount of analyte (the "test samples") are assayed by measuring the amount of test particles and the amount of internal control particles in the detection zone for the test sample, and the concentration of analyte in the test sample is determined by calculating the corrected test sample amount and referring to the standard curve. One standard curve can be generated and used for all test samples, particularly for all test samples in a manufacturer's lot of membranes; it is not necessary that the standard curve be regenerated for each sample. The standard curve is recalibrated for each different detection reagent.

If additional internal control components (control detection reagent, control reaction zone) are used in the assay, the internal control particles which are mobilized by fluid are also moved by capillary action to the control reaction zone, as described above. The internal control particles bind to the control detection reagent in the control reaction zone, generating internal control particle-control detection reagent complexes (herein referred to as "control complexes"). The amount of control complexes in the control reaction zone is detected in the same manner as the amount of test particles in the detection zone. The corrected test particle amount is determined, and the amount of analyte can then be determined using appropriate calculation. For example, in one embodiment, the ratio (Rc) of the corrected test particle amount to the amount of control complexes present in the control reaction zone is determined. The amount of analyte present can be then determined from the ratio, utilizing a standard curve. The standard curve is generated by preparing a series of control samples, containing known concentrations of the analyte of interest in the fluid in which the analyte is to be detected (such as serum depleted of the analyte). The quantitative immunochromatographic assay is then performed on the series of control samples; the value of Rc is measured for each control sample; and the Rc values are plotted as a function of the concentration of analyte included in the control sample. Samples containing an unknown amount of analyte (the "test samples") are assayed by measuring the value of Rc for the test sample, and the concentration of analyte in the test sample is determined by referring to the standard curve. As above, one standard curve can be generated and used for all test samples; it is not necessary that the standard curve be re-generated for each test sample. Alternatively, other ratios and/or standard curves can also be used to determine the amount of analyte in the sample.

In a second embodiment of the invention, the detection zone of the membrane strip, rather than the application point, is contacted with the fluid sample. The membrane strip is maintained under conditions which are sufficient to allow analyte of interest in the fluid sample to bind to the detection reagent in the detection zone, thereby generating immobilized analyte. Subsequently, the application point of the membrane is contacted with water or a buffer. The buffer can be an aqueous fluid that wets the membrane material; that supports a reaction between the analyte of interest and the analyte binding agent (e.g., does not interfere with antibody/antigen interaction); and that has a viscosity that is sufficiently low to allow movement of the fluid by capillary action. Examples of buffers include, for example, saline, or 50 mM Tris-HCl, pH 7.4. The buffer transports the population of test particles and the population of internal control particles imbedded in the membrane at the contact region to the detection zone. The membrane strip is further maintained under conditions which are sufficient to allow the immobilized analyte to interact with the test particles. Interaction of immobilized analyte with test particles arrests the movement of the test particles, and generates arrested analyte-particle complexes. The amount of test particles in the detection zone is then measured, as described above, as is the amount of internal control particles arrested in the detection zone, and the amount of analyte in the fluid sample is determined by determining the amount of corrected test particles, as described above. For example, the amount of analyte of interest in the fluid sample can be related to the corrected test particle amount (e.g., by a standard curve). If desired, the amount can also be determined using additional internal control components, and determining ratios, as described above.

Enzyme-linked Immunosorbent Assay (ELISA) and Other Immunoassays

Although the present invention has been described with respect to quantitative immunochromatographic assays, the methods described herein can be utilized for other types of immunoassays, such as enzyme-linked immunosorbent assays (ELISAs). Generally, an ELISA is a test for an analyte in which a test sample containing analyte is adsorbed on a surface of a solid phase and exposed to a complex of an enzyme linked to a detection reagent that is typically an antibody specific for the analyte being tested for, with a positive result indicated by a treatment yielding a color in proportion to the amount of analyte in the test sample. The analyte and the detection reagent (e.g., an analyte binding agent, such as antibody specific for the analyte) are members of an "immunobinding pair," in which a first member (e.g., analyte) reacts specifically with a second member (e.g., the detection reagent). One or both members of an immunobinding pair can be an antibody. Alternatively, neither the analyte nor the detection reagent are antibodies; however, the analyte and the detection reagent nevertheless form a specific binding pair, in which the first member reacts specifically with the second member.

In a typical ELISA reaction, a first member of an immunobinding pair (e.g., a detection reagent, such as an antibody if an antigen is to be measured, or antigen if an antibody is to be measured or if an inhibition assay is to be performed) is adsorbed or coupled to a surface of a solid phase, such as the well of a microtiter plate. The portion of the surface of that is not covered by the detection reagent is then "blocked" by adsorbing or coupling another material, such as detergent, skim milk, or bovine serum albumin onto the solid surface. The blocking agent is intended to inhibit non-immune (i.e., non-specific) binding of analyte or subsequent reagents; however, blocking reactions are not completely effective, resulting in a positive signal in samples that do not contain analyte. The magnitude of non-specific binding varies from well to well because it depends on the imperfect uniformity of the well surfaces. The solid phase having the first member of the immunobinding pair adsorbed thereon, is then exposed to a solution containing the second member of the immunobinding pair, such as a test sample to be assessed for the presence of analyte of interest. Alternatively, if desired, a test sample to be assessed for the presence of analyte of interest can be adsorbed onto the surface of the solid phase, which is then contacted with a solution containing a detection reagent. In either embodiment, subsequent steps allow detection and quantitation of the amount of interaction between the first and second members of the immunobinding pair.

For example, in a typical ELISA assay, antibody bound to a microtiter plate well is exposed to a test sample containing antigen; subsequently, a washing step with a weak detergent in buffer is performed, and another antibody (the initial detection antibody) which binds to antigen is then added to the plate wells, under conditions in which it binds to the surface-bound antigen. The initial detection antibody may carry the enzyme which is used to catalyze color development, or may also be a bridging antibody to which another antibody-enzyme conjugate is subsequently bound. The initial detection antibodies and/or antibody-enzyme conjugates can displace the blocking material or bind to areas of the plate not protected by binding agent, thereby producing non-specific contribution to the signal.

The methods of the invention correct for non-specific signal by accounting for non-specific binding in every well, rather than by subtracting an average blank value which does not take into account well-to-well-variation. To perform the methods of the invention for an ELISA, the solid phase reactant (e.g., a microtiter plate) having a first member of an immunobinding pair (e.g., a detection reagent) adsorbed thereon is provided; the solid phase reactant is contacted with a sample containing (or to be assessed for the presence of) a second member of the immunobinding pair, such as a sample containing or to be assayed for the presence of an analyte of interest, under conditions which are sufficient to allow interaction between the first and second members of the immunobinding pair (e.g., binding of any analyte of interest present in the sample to the detection agent adsorbed on the solid phase reactant). This contacted solid phase reactant is then contacted with a solution that contains an internal control antibody combined with an initial detection antibody (e.g., as in the wash used for the washing step after the plate is exposed to the test sample), in approximately equal proportions of internal control antibody and initial detection antibody. The internal control antibody is as chemically similar as possible to the initial detection antibody, while still being capable of recognition by a specific reagent independently from the analyte detection reagents. For example, if an anti-analyte mouse monoclonal IgG is used as an initial detection antibody, the internal control antibody can be another mouse monoclonal IgG of another isotype which would react with an isotype-specific antibody. Subsequent steps of the ELISA can then be performed. For example, reagents are added which will detect independently the analyte detection reagents (including the initial detection antibody) and the internal control antibody detection reagents (including the internal control antibody), such as by the use of independent bridging antibodies and/or enzyme-conjugated antibodies that distinguish the parallel reactions. The final antibody-enzyme conjugates are selected to produce distinguishable products from two different substrates (e.g., different colored products). The two products are detected, and amounts of both the initial detection antibody and the internal control antibody bound to each well are determined. The corrected amount of initial detection antibody (that is, the amount of initial detection antibody after taking into consideration the non-specific binding of the internal control antibody) can be determined, as described above. For example, the amount of the internal control antibody bound to the solid phase can be subtracted from the amount of the initial detection antibody bound to the solid phase, producing a corrected signal. The amount of a member of interest of the immunobinding pair (either the first or the second member) can then be determined from the corrected amount of initial detection antibody (or the corrected signal), for example, by using a standard curve.

The invention also includes kits for use in the methods described herein. Kit components can include: buffers, fluid collection means, and control samples for generation of a standard curve; test particles and/or internal control particles; or initial detection antibodies and/or internal control antibodies.

The present invention is illustrated by the following Examples, which are not intended to be limiting in any way.

EXAMPLES

Example 1

Demonstration of Non-specific Particle Accumulation

A quantitative immunochromatographic assay utilizing a rapid antigen measurement platform (RAMP™) apparatus, as described in U.S. Pat. No. 5,753,517, was performed to demonstrate non-specific particle retention. Briefly, the apparatus included a membrane strip of cellulose nitrate; on the membrane were an application point, a contact region, and a detection zone, with the contact region between the application point and the detection zone, and an internal control, which included internal control particles, a control detection reagent, and a control reaction zone. Imbedded in the contact region was a population of organic polymer latex particles (Duke Scientific, Palo Alto, Calif.) coated with a mouse monoclonal antibody to the analyte of interest (myoglobin) (test particles). The particles were labeled, using a fluorescent label, to facilitate detection. Internal control particles, identical in composition to the organic polymer latex particles of the test particles but coated with mouse monoclonal antibody MOPC31-c (Sigma, St. Louis, Mo.) having an unknown specificity were also imbedded in the contact region; equal amount of test particles and internal control particles were mixed and dried onto the membrane at the contact region. The internal control particles were also labeled using a fluorescent label, which was different from the fluorescent label of the test particles. The detection reagent immobilized in the detection zone was polyclonal anti-myoglobin antibody preparation from goat serum; the control detection reagent immobilized in the control reaction zone was polyclonal antibody preparation from goat serum directed against mouse IgG.

To conduct the assay, an application pad covering and in contact with the application point of the membrane strip was contacted with various samples of buffered 3% BSA to be assayed for the presence and amount of myoglobin. Samples were spiked with 0 or 20 ng/ml myoglobin, and 3 to 10 samples for each batch were run. After contact of the sample at the application point, he apparatus was then maintained under conditions which allowed capillary action of fluid through the membrane strip to the contact region, transporting myoglobin (if present in the sample) to the contact region so that it could bind to the antibody-coated particles imbedded in the contact region, mobilizing the test particles and the internal control particles, and moving the particles through the membrane, past the detection zone and the control reaction zone. The amount of test particles that arrested in the detection zone, and the amount of internal control particles that arrested in the control reaction zone, were then detected. The ratio of the test particle concentration at the detection zone, to the internal control particle concentration at the control reaction zone, can be referred to a standard curve to provide the analyte concentration. The results are shown in Table 1, below.

It can be seen from Table 1 that in the samples containing no myoglobin, there is nevertheless a significant accumulation of test particles at the detection zone, as indicated by the average Ctt value. Since there was no antigen in the buffered BSA solution in the samples with no myoglobin, there could be no specific arrest of the test particles at the detection zone, thereby implying that approximately half a million particles were captured non-specifically at this location. Scans of the entire length of each membrane strip showed that no significant concentration of particles was present in the regions adjacent to the detection zone and the control reaction zone, where no antibodies was dried on the membrane. Thus the non-specific arrest was due to nonimmune effects on the particles by the dried polyclonal antisera at the detection zone and the control reaction zone. The non-specific arrest could be caused by a variety of mechanisms. For example, particles could be trapped in the interstices of the membrane fibers, in spite of the particle size being much smaller than the effective pore size of the membrane. Most membranes used in such immunochromatography assays consist of irregular beds of fibers whose separations vary greatly throughout the membranes. Near locations where fibers cross, there are regions with sufficiently small separation to trap even small particles; this trapping may be enhanced when protein is dried onto the fibers, because of alterations in the effective pore size caused by the dried proteins. In addition, adsorption of particles to unblocked fiber surfaces can occur. Furthermore, any particle aggregation exacerbates size-dependent trapping, so the larger

TABLE 1

Accumulation of non-specifically bound particles

| [Mb] ng/ml | n | Avg Ctt (n strips) | Avg Cst (n strips) | [Mb] ng/ml | n | Avg Ctt (n strips) | Avg Cst (n strips) |
| --- | --- | --- | --- | --- | --- | --- | --- |
| 0 | 5 | 0.384 | 0.676 | 20 | 5 | 1.34 | 0.753 |
| 0 | 5 | 0.382 | 0.628 | 20 | 5 | 1.24 | 0.722 |
| 0 | 10 | 0.349 | 0.230 | 20 | 10 | 1.01 | 0.193 |
| 0 | 3 | 0.512 | 0.324 | 20 | 3 | 1.08 | 0.405 |
| 0 | 3 | 0.621 | 0.411 | 20 | 3 | 1.19 | 0.528 |
| 0 | 3 | 0.331 | 0.365 | 20 | 3 | 0.994 | 0.511 |

TABLE 1-continued

Accumulation of non-specifically bound particles

| [Mb] ng/ml | n | Avg Ctt (n strips) | Avg Cst (n strips) | [Mb] ng/ml | n | Avg Ctt (n strips) | Avg Cst (n strips) |
| --- | --- | --- | --- | --- | --- | --- | --- |
| 0 | 3 | 0.364 | 0.336 | 20 | 3 | 0.716 | 0.335 |
| 0 | 3 | 0.345 | 0.311 | 20 | 3 | 0.727 | 0.303 |
| 0 | 3 | 0.487 | 0.294 | 20 | 3 | 0.967 | 0.436 |
| 0 | 3 | 0.715 | 0.557 | 20 | 3 | 1.08 | 0.405 |
| 0 | 3 | 0.512 | 0.324 | 20 | 10 | 1.01 | 0.193 |
| 0 | 10 | 0.349 | 0.230 | 20 | 10 | 1.05 | 0.293 |
| 0 | 10 | 0.503 | 0.250 | | | | |
| 0 | 3 | 0.805 | 0.778 | | | | |
| 0 | 3 | 0.560 | 0.613 | | | | |
| 0 | 3 | 0.517 | 0.544 | | | | |
| 0 | 3 | 0.517 | 0.532 | | | | |
| 0 | 3 | 0.540 | 0.760 | | | | |
| 0 | 3 | 0.410 | 0.480 | | | | |
| 0 | 3 | 0.590 | 0.620 | | | | |
| 0 | 3 | 0.406 | 0.430 | | | | |
| 0 | 3 | 0.733 | 0.869 | | | | |
| AVG | | 0.497 | 0.480 | | | 1.030 | 0.423 |
| S.D. | | 0.135 | 0.190 | | | 0.183 | 0.182 |
| t-test | | | n.s. | | | | n.s. different |

Ctt=number of test particles accumulated at the detection zone; Cst=number of internal control particle accumulated at the detection zone; S.D.=standard deviation; n.s.=no significant difference at the 5% level. Both Ctt and Cst are in units of millions of particles. the aggregation, the more the trapping. Particles already arrested will also decrease the effective pore size locally, increasing the degree of non-specific trapping. Also, time and ambient conditions (temperature, humidity) will effect the rate of reaction for each membrane.

The values of Cst for the no myoglobin samples (Mb=0) report the number of internal control particles also arrested at the detection zone. It can be seen that the ensemble average for Cst does not differ significantly (Student t test) from that for Ctt; therefore, the Cst value provides a valid estimate of the non-specific arrest of the test particles in the absence of antigen. In the presence of antigen, non-specific arrest of test particles must also occur. If the arrest were constant from strip to strip, it might be possible to correct for it by subtracting an average "blank" value; however, an average blank value does not take into consideration many factors which will influence the reaction for each strip, and therefore does not provide a reliable correction for non-specific particle arrest. For example, membrane strips do not exhibit uniformity, and the arrest therefore will not be constant from strip to strip. The lack of uniformity occurs because of the large scale on which membranes are made: it is not possible to control membrane properties precisely over distances of less than 1 cm (the order of magnitude of the width of standard test strips). Moreover, complex samples (e.g., those of biological origin) can contain hundreds of macromolecular species, some of which are capable of causing particle aggregation in spite of blocking reactions carried out when particles are coated with antibodies. Hence, variable degrees of aggregation can occur in different test strips; aggregation can cause varying degrees of non-specific particle arrest at the detection zone, thereby producing a signal that will interfere with accurate interpretation of the amount of signal (and thus, the amount of analyte) at the reaction zone.

EXAMPLE 2

Correction for Non-Specific Particle Accumulation

In order to correct for non-specific particle arrest at the detection zone, the behavior of the internal control particle population is used to provide a measure of the nonspecific arrest of the test particle population.

To confirm that the Cst value (the number of internal standard particles accumulated at the detection zone) provides a good approximation for the amount of non-specific arrest of test particles at the reaction zone in the presence of measurable amounts of antigen, antigen (20 ng/ml of myoglobin) was added to buffered BSA solutions, and the assays were run as described above. The results, shown in Table 1 above, demonstrated that the ensemble average value of Ctt (number of test particles accumulated at the detection zone) was much larger than the value at Mb=0, but that the average value of Cts was not significantly different from its value at Mb=0. Thus, Cts provides a good measure of the amount of non-specific arrest of test particles at the detection zone in the presence of measurable amounts of antigen.

To evaluate the non-specific arrest of test particles in a complex biological sample, whole blood samples from four donors were evaluated. RAMP assays for myoglobin were run on whole blood samples, and on whole blood samples into which 100 ng/ml of myoglobin had been spiked. The values for the number of particles of each type (test particles, internal control particles) arrested at the detection zone and at the control reaction zone were assessed, and then the values were analyzed in three ways.

Calculation by Ratio of Test Particles to Internal Control Particles

First, as described in U.S. Pat. 5,753,517, the number of test particles at the detection zone (Ctt), was divided by the number of internal standard particles arrested at the internal control line (Css), to form the ratio Rq for each membrane strip. Data for a standard curve was generated by preparing a series of solutions of buffered 3% BSA spiked with various levels of Mb, performing RAMP assays, and generating a standard curve by plotting the values of Rq vs [Mb] (concentration). The curve was then used to convert the values of Rq for each sample of the whole blood assay into [Mb]. Because normal blood contains a significant, but unknown, concentration of Mb, the Mb content of the samples to which no Mb was added were estimated from their assays, and the values subtracted from the estimates obtained from the spiked samples. The value thus determined, expressed as a fraction of the concentration with which the sample was spiked, is the "recovery" amount. Results are shown in Table 2.

TABLE 2

Recovery Amounts of Myoglobin Calculated from Rq = Ctt/Css

| Donor (n = 5 per donor) | Mean | SD | CV |
|---|---|---|---|
| WH | 759% | 704% | 93% |
| MW | 203% | 148% | 73% |
| PH | 212% | 84% | 40% |
| JH | 204% | 25% | 12% |
| Average | 545% | 240% | 54% |
| SD | 277% | 313% | 36% |

Recovery calculated from Rq=Ctt/Css.

The results from Table 2 demonstrate that Rq ratio alone provides a large overestimate (over a factor of 5), of the amount of myoglobin added to the samples. This is because there is no correction for non-specific arrest of test particles at the detection zone.

Subtraction of "Blank Value" from Ctt Estimate

A common way to correct for non-specific accumulation is to subtract a blank value from the Ctt estimate for each assay. Such a calculation is shown in Table 3.

TABLE 3

Recovery Amounts of Myoglobin Calculated from Ro = (Ctt − Ctto)/Css

| Donor (n = 5 per donor) | Mean | SD | CV |
|---|---|---|---|
| WH | 678% | 1416% | 209% |
| MW | 95% | 34% | 35% |
| PH | 114% | 31% | 27% |
| JH | 117% | 10% | 9% |
| Average | 251% | 373% | 70% |
| SD | 285% | 696% | 93% |

Ctto is the average value of Ctt, in units of millions of particles, for 5 Mb-free samples run in buffered 3% BSA as described above.

For this correction, the average value of Ctt measured for the [Mb]=0 assays, that was generated as part of the standard curve determination (Ctto), was subtracted from each value of Ctt before forming the ratio with Css as described above. The ratio, Ro, was calculated from the data generated for the standard curve and the curve was used as a reference for calculation of "recovery" as described above. As shown in Table 3, use of the blank correction value improves the results, but average recovery is still more than twice the spiked value.

Subtraction of Internal Control Particle Value

When the number of internal control particles non-specifically arrested at the test line (Cst), is subtracted from Ctt for each strip, and the difference used in the ratio with Css, the recovery averages 96%, as shown in Table 4.

TABLE 4

Recovery Amounts of Myoglobin Calculated from Rc = (Ctt − Cst)/Css.

| Donor (n = 5 per donor) | Mean | SD | CV |
|---|---|---|---|
| WH | 46% | 44% | 95% |
| MW | 90% | 48% | 54% |
| PH | 133% | 38% | 28% |
| JH | 115% | 18% | 15% |
| Average | 96% | 37% | 48% |
| SD | 38% | 14% | 35% |

These results demonstrate that subtraction of the amount of internal control particles arrested in the detection zone provides a simple way to correct for non-specific interferences in solid phase immunoassays.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of measuring the amount of a member of an immunobinding pair in a sample, comprising:
   a) providing a solid phase reactant having a first member of an immunobinding pair absorbed thereon;
   b) the contacting solid phase reactant with the sample to be assayed for the amount of a second member of the immunobinding pair, under conditions which allow binding of the second member of the immunobinding pair, if present in the sample, to the first member of the immunobinding pair absorbed on the solid phase reactant, thereby forming a contacted solid phase reactant;

c) contacting the contacted solid phase reactant with a solution comprising initial detection antibody and internal control antibody, under conditions which allow the initial detection antibody and to bind to the second member of the immunobinding pair that is bound to the first member of the immunobinding pair adsorbed on the solid-phase reactant and to allow non-specific binding of the internal control antibody to the solid phase reactant;

d) determining the amount of initial detection antibody and the amount of internal control antibody on the solid phase reactant using detection reagents which allow independent detection of the initial detection antibody and the internal control antibody; and e) determining a corrected amount of initial detection antibody by compensating for the amount of non-specific binding of the internal control antibody to the solid phase reactant, wherein the amount of the second member of the immunobinding pair in the sample is related to the corrected amount of initial detection antibody.

2. The method of claim 1, wherein the corrected amount of initial detection antibody is equal to the difference between the amount of initial detection antibody on the solid phase reactant and the amount of internal control antibody on the solid phase reactant.

3. The method of claim 1, wherein the first member of the immunobinding pair is an analyte of interest, and the second member of the immunobinding pair is an antibody to the analyte of interest.

4. The method of claim 1, wherein the second member of the immunobinding pair is an analyte of interest, and the first member of the immunobinding pair is an antibody to the analyte of interest.

5. A method for measuring the amount of a member of an immunobinding pair in a sample, comprising:

a) providing a solid phase reactant having adsorbed thereon a sample to be assayed for the amount of a first member of an immunobinding pair;

b) contacting the solid phase reactant with a second member of the immunobinding pair, under conditions which allow binding of the first member of the immunobinding pair, if present in the sample, to the second member of the immunobinding pair, thereby forming a contacted solid phase reactant;

c) contacting the contacted solid phase reactant with a solution comprising initial detection antibody and internal control antibody, under conditions which allow the initial detection antibody to bind to the second member of the immunobinding pair adsorbed on the solid-phase reactant and to allow non-specific binding of the internal control antibody to the solid phase reactant;

d) determining the amount of initial detection antibody and the amount of internal control antibody on the solid phase reactant using detection roagents which allow independent detection of the initial detection antibody and the internal control antibody; and e) determining a corrected amount of initial detection antibody by compensating for the amount of non-specific binding of the internal control antibody to the solid phase reactant, wherein the amount of first member of the immunobinding pair in the sample is related to the corrected amount of initial detection antibody.

6. The method of claim 5, wherein the corrected amount of initial detection antibody is equal to the difference between the amount of initial detection antibody on the solid phase reactant and the amount of internal control antibody on the solid phase reactant.

7. The method of claim 5, wherein the first member of the immunobinding pair is an analyte of interest, and the second member of the immunobinding pair is an antibody to the analyte of interest.

8. The method of claim 5, wherein the second member of the immunobinding pair is an analyte of interest, and the first member of the immunobinding pair is an antibody to the analyte of interest.

* * * * *